US011529459B1

(12) United States Patent
Schiff et al.

(10) Patent No.: US 11,529,459 B1
(45) Date of Patent: Dec. 20, 2022

(54) WEARABLE INJECTOR WITH ADHESIVE MODULE

(71) Applicant: Fresenius Kabi Deutschland GmbH, Bad Homburg (DE)

(72) Inventors: David R. Schiff, Highland Park, NJ (US); Justin Bechstein, Philadelphia, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/246,297

(22) Filed: Apr. 30, 2021

(51) Int. Cl.
*A61M 5/142* (2006.01)
*A61B 5/00* (2006.01)
*A61L 24/06* (2006.01)

(52) U.S. Cl.
CPC .......... *A61M 5/14248* (2013.01); *A61L 24/06* (2013.01)

(58) Field of Classification Search
CPC ............. A61M 5/14248; A61B 5/6833; A61B 2046/205; A61F 15/004
See application file for complete search history.

(56) References Cited

U.S. PATENT DOCUMENTS

| | | |
|---|---|---|
| 2003/0167036 A1 | 9/2003 | Flaherty |
| 2004/0116866 A1* | 6/2004 | Gorman ............ A61M 5/14248 604/174 |
| 2004/0199123 A1 | 10/2004 | Nielsen |
| 2008/0091139 A1 | 4/2008 | Srinivasan et al. |
| 2008/0125700 A1 | 5/2008 | Moberg et al. |
| 2008/0269657 A1* | 10/2008 | Brenneman ............ A61B 46/10 602/41 |
| 2009/0131860 A1 | 5/2009 | Nielsen |
| 2010/0137832 A1 | 6/2010 | Mathews et al. |
| 2010/0262078 A1 | 10/2010 | Blomquist |
| 2011/0060196 A1* | 3/2011 | Stafford ............... A61B 5/6833 600/309 |
| 2011/0178461 A1 | 7/2011 | Chong et al. |
| 2012/0010594 A1 | 1/2012 | Holt et al. |
| 2015/0374919 A1 | 12/2015 | Gibson |
| 2016/0038689 A1 | 2/2016 | Lee et al. |
| 2016/0082182 A1 | 3/2016 | Gregory et al. |
| 2016/0199574 A1 | 7/2016 | Ring et al. |
| 2016/0220798 A1 | 8/2016 | Netzel et al. |
| 2016/0296704 A1 | 10/2016 | Gibson |
| 2016/0354555 A1 | 12/2016 | Gibson et al. |

(Continued)

FOREIGN PATENT DOCUMENTS

| | | |
|---|---|---|
| WO | 2018081234 A1 | 5/2018 |
| WO | 2018183039 A1 | 10/2018 |

(Continued)

OTHER PUBLICATIONS

RightCare CGM Adhesive Universal Overpatches; Amazon. Available for sale May 6, 2020. https://www.amazon.com/Adhesive-Universal-Covered-Synthetic-Extreme/dp/B083QMYXQ7/ref=sr_1_27?keywords=overpatch&qid=1639080153&sr=8-27&th=1 (Year: 2020).*

(Continued)

*Primary Examiner* — Laura A Bouchelle
(74) *Attorney, Agent, or Firm* — Cook Alex Ltd.

(57) ABSTRACT

An on-body drug delivery device having a housing carried by a substrate. The device includes an adhesive module placed over at least a portion of said device to provide added securement of the device to the patient's body.

18 Claims, 8 Drawing Sheets

(56) References Cited

U.S. PATENT DOCUMENTS

| | | |
|---|---|---|
| 2017/0119969 A1 | 5/2017 | McCullough et al. |
| 2017/0124284 A1 | 5/2017 | McCullough et al. |
| 2017/0147787 A1 | 5/2017 | Albrecht et al. |
| 2017/0182253 A1 | 6/2017 | Folk et al. |
| 2017/0340837 A1 | 11/2017 | Nazzaro et al. |
| 2017/0361015 A1 | 12/2017 | McCullough |
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0009019 A1 | 1/2019 | Shor et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani et al. |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0261643 A1 * | 8/2020 | Boyaval ............ A61M 5/14248 |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

OTHER PUBLICATIONS

Omnipod Grip Shield Designed by Deck My Diabetes; Amazon. Available for sale Dec. 14, 2020. https://www.amazon.com/Deck-My-Diabetes-Flexible-Additional/dp/B08QL3TVZB/ref=sr_1_6?keywords=insulin+pump+overlay&qid=1639074568&sr=8-6 (Year: 2020).*

Dexcom G6: Reusable Infiniflex Protective Overlay Guard Flexible Armor Case Cover. Etsy.com. https://www.etsy.com/shop/OldsNewAgain?ref=simple-shop-header-name&listing_id=1081102727 (Year: 2021).*

* cited by examiner

WEARABLE INJECTOR WITH ADHESIVE MODULE

FIELD OF THE DISCLOSURE

The present disclosure relates to drug delivery/infusion devices. More particularly, the present disclosure relates to devices mounted to the body for automatically delivering a drug to a patient. Even more particularly, the present disclosure relates devices mounted to the body of a patient, the device including a substrate including an adhesive for securing the substrate to the body of the patient and a second device including an adhesive for providing added adhesion of the device to the body of the patient.

DESCRIPTION OF RELATED ART

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

Figure 1:
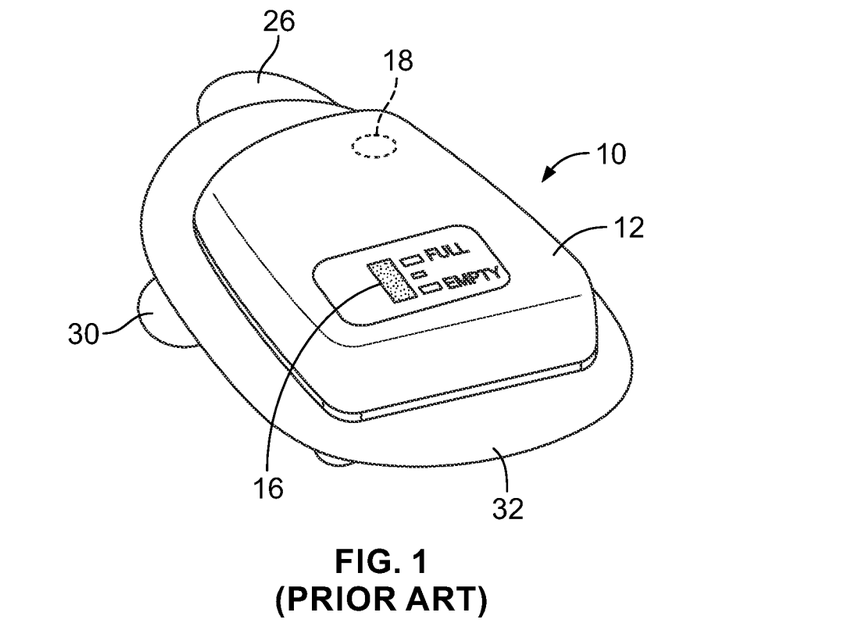
FIG. 1 is a top perspective view of a drug delivery device according to conventional design.
Figure 2:
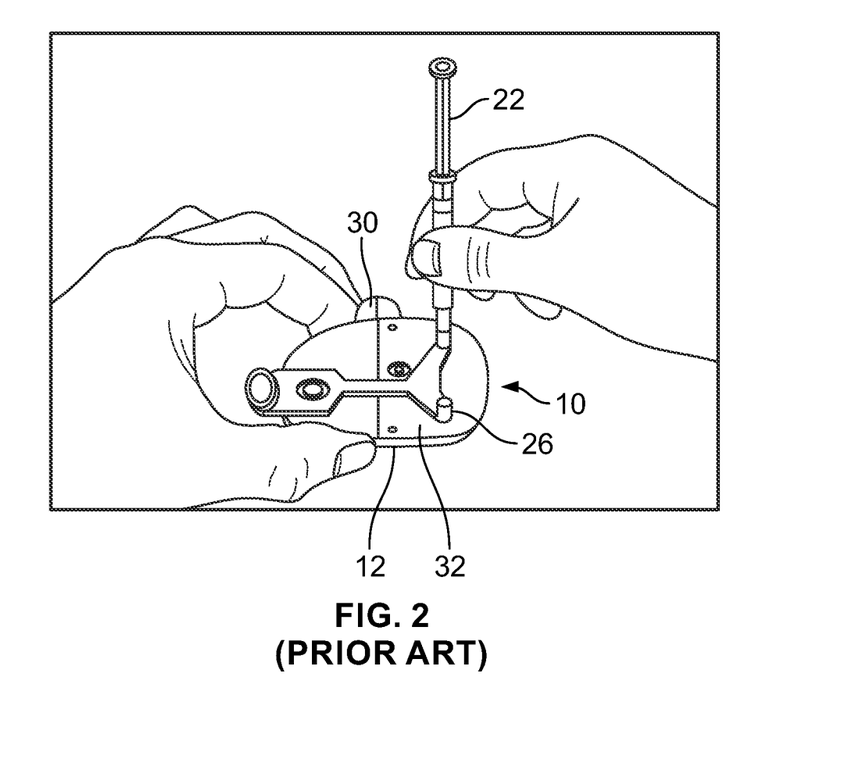
FIG. 2 is a bottom perspective view of the drug delivery device of FIG. 1.
Figure 3:
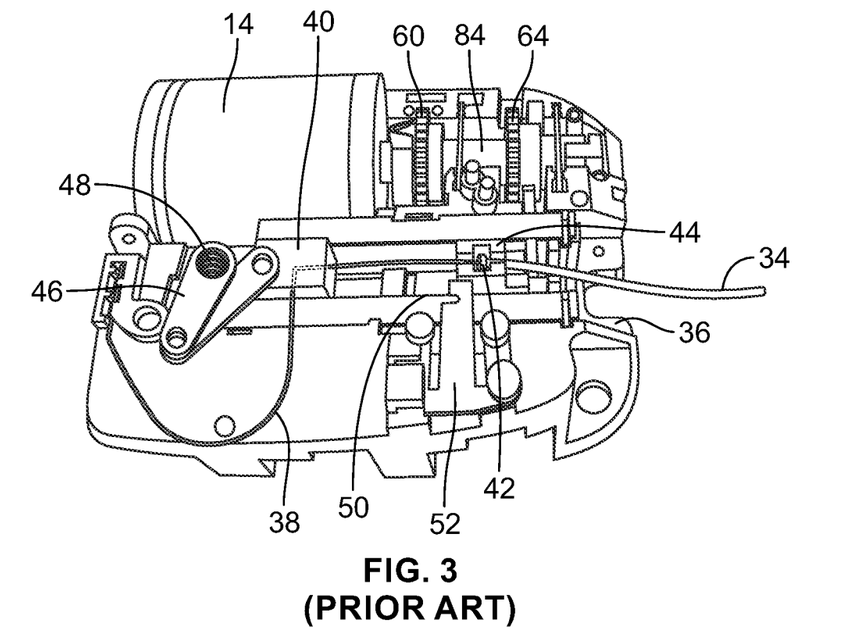
FIG. 3 is a top perspective view of the interior components of the drug delivery device of FIG. 1.
Figure 4:
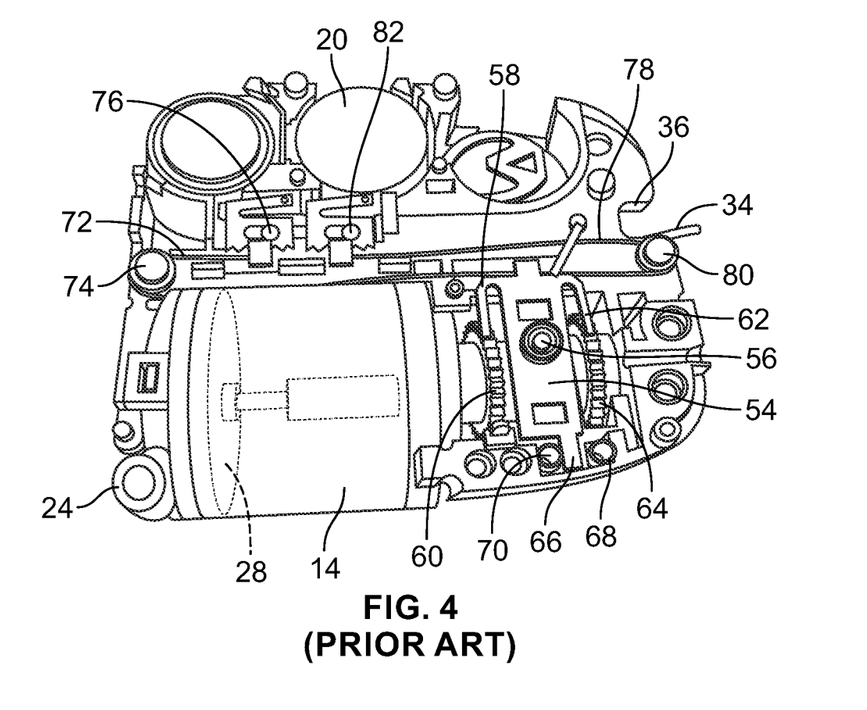
FIG. 4 is a bottom perspective view of the interior components of the drug delivery device of FIG. 1.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provide power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 (substrate) associated with the underside of the housing 12. The housing 12 is then pressed against the body of the patient, with the adhesive pad 32 (adhesive side of the substrate) facing the body. An adhesive present on the adhesive pad/substrate 32 causes the adhesive pad 32 (and, hence, the housing 12) to adhere to the body. Examples of devices using adhesive pads/substrates are described in U.S. Patent Application Publication 2019/0083702 and International Patent Application Publication WO2018/081234, the contents of which are incorporated by reference herein in their entireties.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with gears 60 and 64 as a singled, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there remains room for improvement. For example, while the substrate that carries the device also secures the device to the patient's skin, additional points of attachment may be desired. In that regard, it would be beneficial to provide an additional means for securing the device to the body of the patient which can preferably be replaced and/or refreshed without removing the device.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, the present disclosure is directed to an on-body drug delivery device including a housing with a cover and a bottom wall. The on-body drug delivery device includes a substrate made of a sheet of flexible material having a top surface and a bottom surface. The housing is carried by the substrate. The bottom of surface of the substrate includes an adhesive applied thereto. The on-body drug delivery device further includes an adhesive module disposed over at least a portion of the device. The adhesive module includes an adhesive on the bottom surface thereof.

In another aspect, the adhesive module includes a film of flexible material having a top surface and a bottom surface, and a second adhesive applied to the bottom surface of said film.

In a further aspect, the adhesive module includes a support for the film.

In a more particular aspect, the support includes an internal frame.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 5:
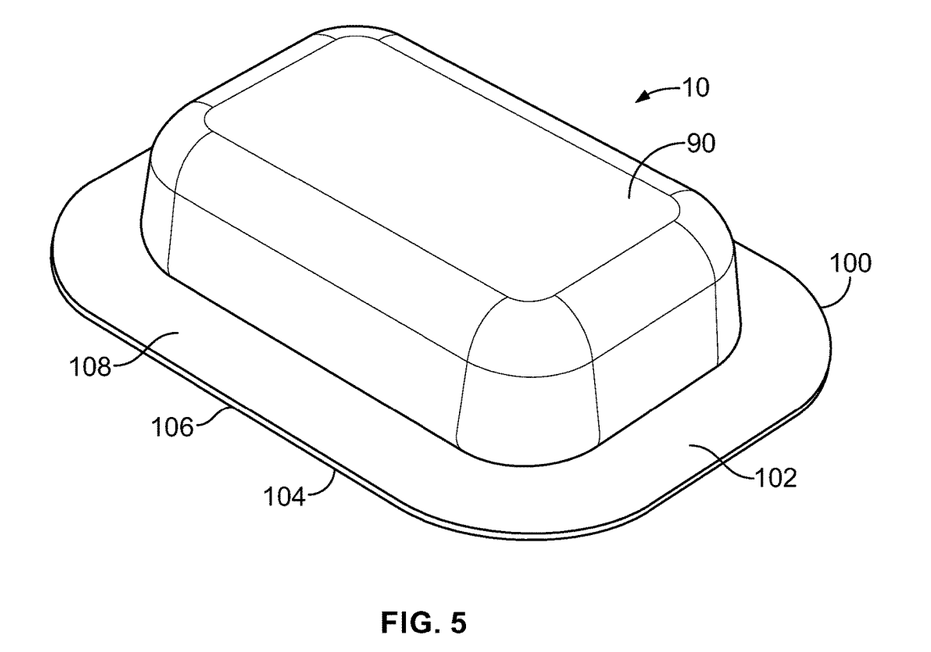
FIG. 5 is a perspective view of a drug delivery device for use in combination with the adhesive modules described herein.

In keeping with the present disclosure, and with reference to FIG. 5, the wearable "on-body" drug delivery/infusion device 10 (which may have a modular construction) comprises a main body or housing 90 that houses many of the electro-mechanical components of the device and a removable cartridge that is pre-filled and/or refillable with a drug. A removable cartridge (not shown) permits re-filling and reuse of the infuser without having to remove it from the patient after the initial attachment and permits the device to be used to deliver more than one type of drug. A separable pre-filled cartridge also facilitates storage of the drug (which would be refrigerated) apart from the main body/housing 90, which may be stored at room temperature, thus reducing the amount of refrigerated storage space required. The cartridge further comprises a pre-filled drug chamber, a piston/plunger, and a structure for pressurizing the drug held within the chamber for delivery to the patient. While a removable cartridge may be advantageous, it is also within the scope of the present disclosure for the device to be provided as a single-use item, with a pre-filled or fillable drug chamber or reservoir, as in conventional devices.

Housing 90 is affixed to and carried by a substrate 100 which may be affixed or adhered to the patient's body. As shown in FIG. 5, substrate 100 may take the form of a flat sheet or pad having a top surface 102 and a bottom surface 104 and further defined by a peripheral edge 106. Substrate 100 may have a rectangular shape with rounded corners, as shown in FIG. 5, or any other suitable shape and size that can accommodate housing 90. In this regard, it may be preferable that substrate 100 includes a dimension, such as surface area, that is greater than the surface area of a bottom wall of housing 90, thereby defining a perimeter 108 between the outside edge of housing 90 and peripheral edge 106 of substrate 100.

Substrate 100 is preferably made of a flexible, resilient material that can be stretched. Substrate 100 may further include upper and lower bacteria impermeable liners as described in US Patent Application Publication No. 2019/0083702, the contents of which are incorporated herein by reference. The exposed surface of peripheral edge may likewise include and be covered by a bacterial impermeable liner.

The flexible, resilient material of substrate 100 may be any such material that can be safely applied and adhered to the skin of the patient. Typically, substrate 100 is made of non-woven, fibrous material. Examples of suitable materials include polyethylene, polyvinyl chloride, polyurethane, polyethylene terephthalate, polypropylene, viscose/rayon, thermoplastic elastomer and the like.

Figure 6A:
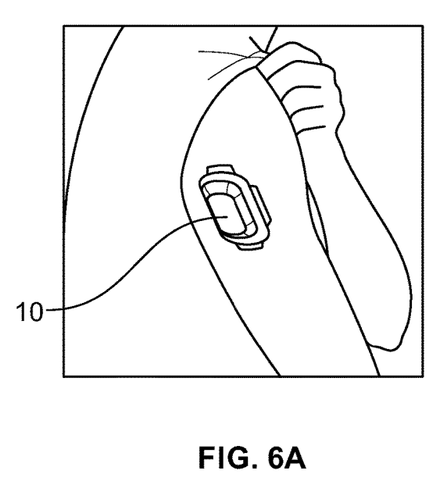
FIG. 6A is an illustration showing the placement of a drug delivery device on the body of a patient.
Figure 6B:
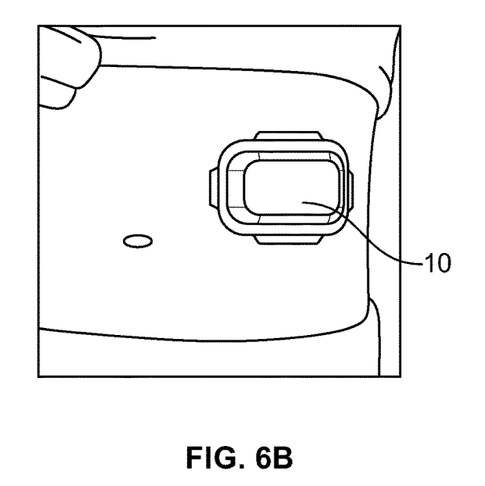
FIG. 6B is an illustration showing an alternative placement of a drug delivery device on the body of a patient.

As shown in FIGS. 6A and 6B, drug delivery device 10 may be worn by the patient (on, for example, the arm or torso) where it is affixed or adhered to the skin of the patient. In one embodiment, substrate 100 may include or be otherwise provided with an adhesive on bottom surface 104. The adhesive is such that the substrate remains adhered to the patient's body and, preferably, cannot be easily dislodged or separated from the patient's skin. In that regard, the adhesive should be waterproof and/or resistant to degradation by perspiration. In addition, adhesive substrate 100 should tightly conform to the skin of the patient to keep the needle of the device from dislodging. At the same time, the adhesive is not permanent and, when necessary, can be removed routinely by a medical professional in an "outpatient" procedure or even by the patient. Examples of suitable adhesives useful with substrates of the type described herein include any medical-grade or skin contact adhesives such as, but not limited to, acrylic or acrylate compositions, synthetic rubber, hydrocolloid, silicone and the like.

In accordance with the present disclosure, device 10 may be provided with a separate adhesive module for securing device 10 to the body of the patient. Using an adhesive module of the type described herein in combination with a device that already includes an adhesive on the bottom surface of a substrate provides an added degree of confidence that device 10 will remain secured during the duration of the drug delivery. In the event that device 10 does become partially dislodged from the skin of the patient, adhesive modules of the type described herein ensure that the device will remain in contact with the patient. Adhesive modules of the type described herein may also help prevent leakage caused by partial dislodgement of device 10. Using a "dual adhesive" approach (i.e., adhesive on the substrate 100 and a second adhesive on the adhesive module) allows for replacement or a refreshment of the adhesive module without having to remove device 10. A dual adhesive approach may also require less adhesive on device substrate 100, making ultimate removal of device 10 from the skin easier on the patient.

Figure 7:
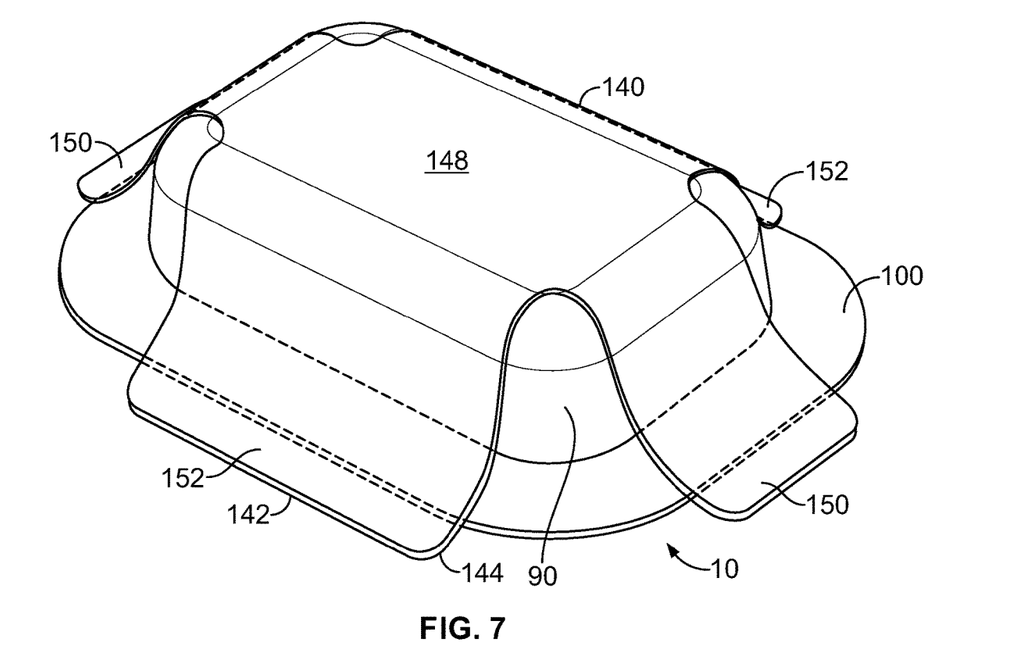
FIG. 7 is a perspective view of a drug delivery device with an embodiment of an adhesive module in accordance with the present disclosure.

Turning now to FIG. 7, a first embodiment of adhesive module 140 is shown. As shown in FIG. 7, adhesive module 140 may be an "over adhesive" member that is applied over and on top of at least a portion of device 10, including housing 90 and substrate 100. In the embodiment of FIG. 7, adhesive module 140 may be a sheet of stretchable adhesive film 142 placed over device 10 and secured to device 10 at selected points. Film 142 may be sized and shaped such that it can be stretched to extend beyond the perimeter 108 of substrate 100 and attach to the skin of the patient. In that regard, bottom surface 144 of film 142 may include an adhesive layer or coating.

As noted above, adhesive module 140 may be sized and shaped to cover at least a portion of device 10 and extend beyond the perimeter 108 of substrate 100 for adhesive attachment to the skin of the patient. In the embodiment of FIG. 7, adhesive module 140 is shown as a cross-shaped sheet with a central portion 148 placed over (and adhered to) housing 90 with end tab portions 150 and side tab portions 152 extending from the central portion 148 over and beyond substrate perimeter 108. During placement, tab portions 150 and 152 may be pulled and stretched to attach adhesive module 140 to the skin of the patient. Of course, it will be understood that the adhesive modules described herein may have other shapes and configurations (such as an oval, rectangle, diamond, or even multiple strips or pieces) provided that, when applied over device 10, they extend beyond the perimeter 108 of substrate 100 to allow for contact with the patient's skin.

Figure 8:
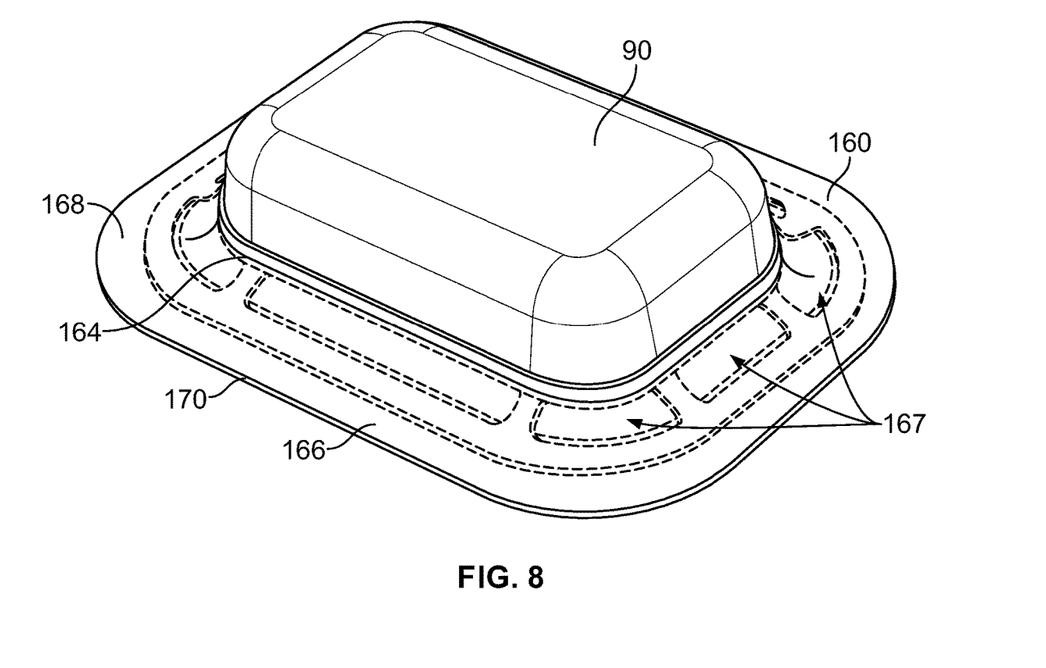
FIG. 8 is a perspective view of a drug delivery device with another embodiment of an adhesive module in accordance with the present disclosure.
Figure 9:
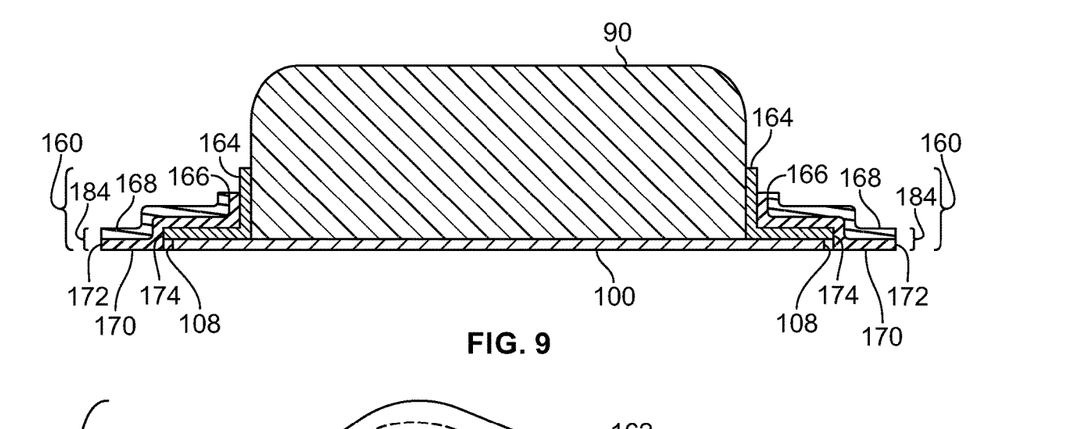
FIG. 9 is a cross-sectional side view of the drug delivery device with the adhesive module of FIG. 8.
Figure 10:
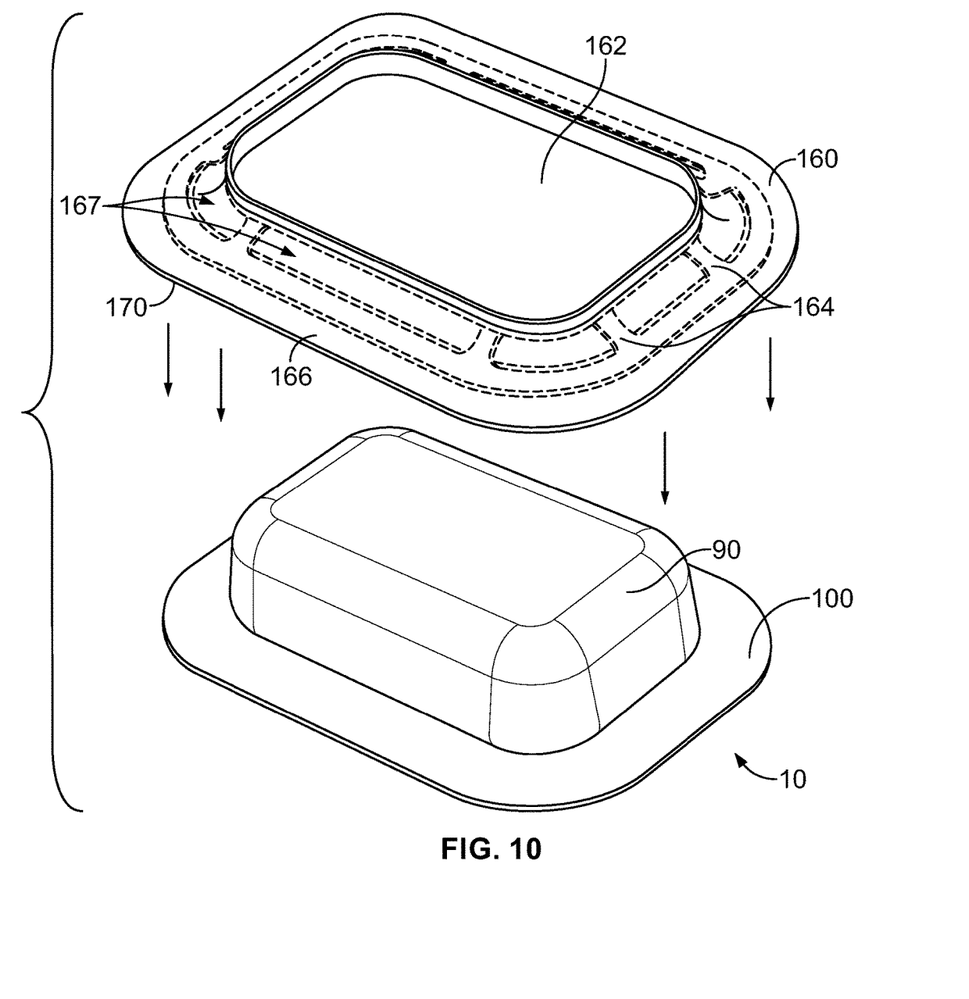
FIG. 10 is an exploded view of the drug delivery device with the adhesive module of FIG. 8.

FIGS. 8-10 show an alternative embodiment of an adhesive module in accordance with the present disclosure. Adhesive module 160 of FIGS. 8-10 is a ringed member that defines a central opening 162 for receiving a portion of device 10. In the case of FIG. 8, central opening 162 is sized and shaped to receive housing 90 of device 10. Adhesive module 160 may be an overlay that is placed over drug delivery device 10, as best seen in FIG. 10. Central opening 162 may be configured such that housing 90 fits snugly within the central opening.

Adhesive module 160 may further include a support member or structure 164 to better align module 160 with drug delivery device 10 and/or to provide a surface to which drug delivery device 10 may be releasably attached by, for example snap-fit, press-fit or detent engagement. Accordingly, support structure 164 is preferably made of a sufficiently rigid material including, but not limited to, plastic polymers such as polyvinyl chloride (PVC), polypropylene, polycarbonate and polystyrene. As shown in FIG. 8 and FIG. 10, support structure 164 may be a rigid frame or framework defining openings 167 therein. Support structure 164 may also be a screen or lattice-like structure or a solid ring to which an adhesive film is attached, as will be described below. Support structure 164 may be injection molded or may be assembled from a plurality of sealed-together porous or solid sheets to form a composite structure having the desired rigidity to receive and align with drug delivery device 10.

Adhesive module 160 further includes an adhesive film 166 attached (adhered) and conformed to support structure 164 as shown in FIGS. 8-10 to provide a single module. Adhesive film 166 includes a top non-adhesive surface 168 and a bottom surface 170 with adhesive applied thereon as a coating or layer 172 of adhesive as shown in FIG. 9. As also shown in FIG. 9, film 166 is conformed to support structure 164 with bottom surface 170 adhered to the solid or rigid portion of support structure 164. Film 166 extends beyond the peripheral edge 174 of structure 164 and, once device 10 is attached to the patient, beyond the outer edge of perimeter 108 where adhesive module 160 can be directly adhered to patient's skin as shown in FIG. 9.

Figure 11:
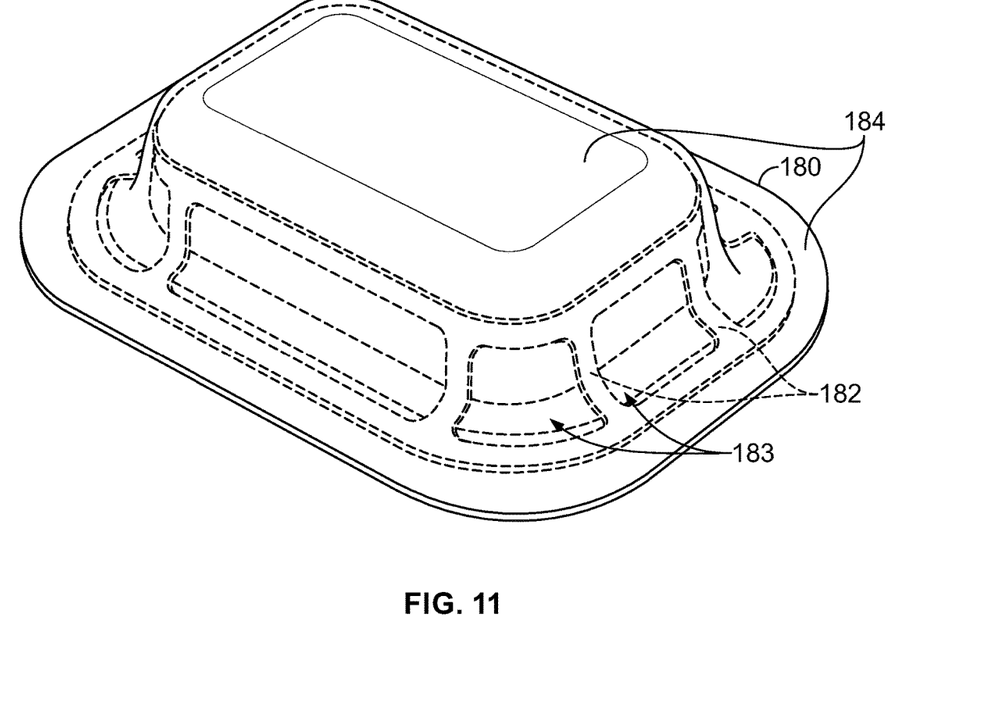
FIG. 11 is a perspective view of a drug delivery device with another embodiment of an adhesive module in accordance with the present disclosure.
Figure 12:
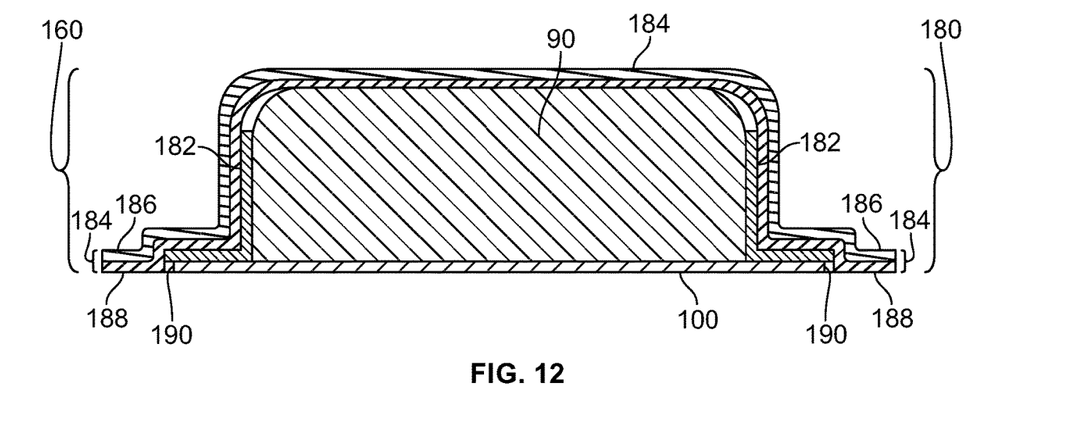
FIG. 12 is a cross-sectional side view of the drug delivery device with the adhesive module of FIG. 11.
Figure 13:
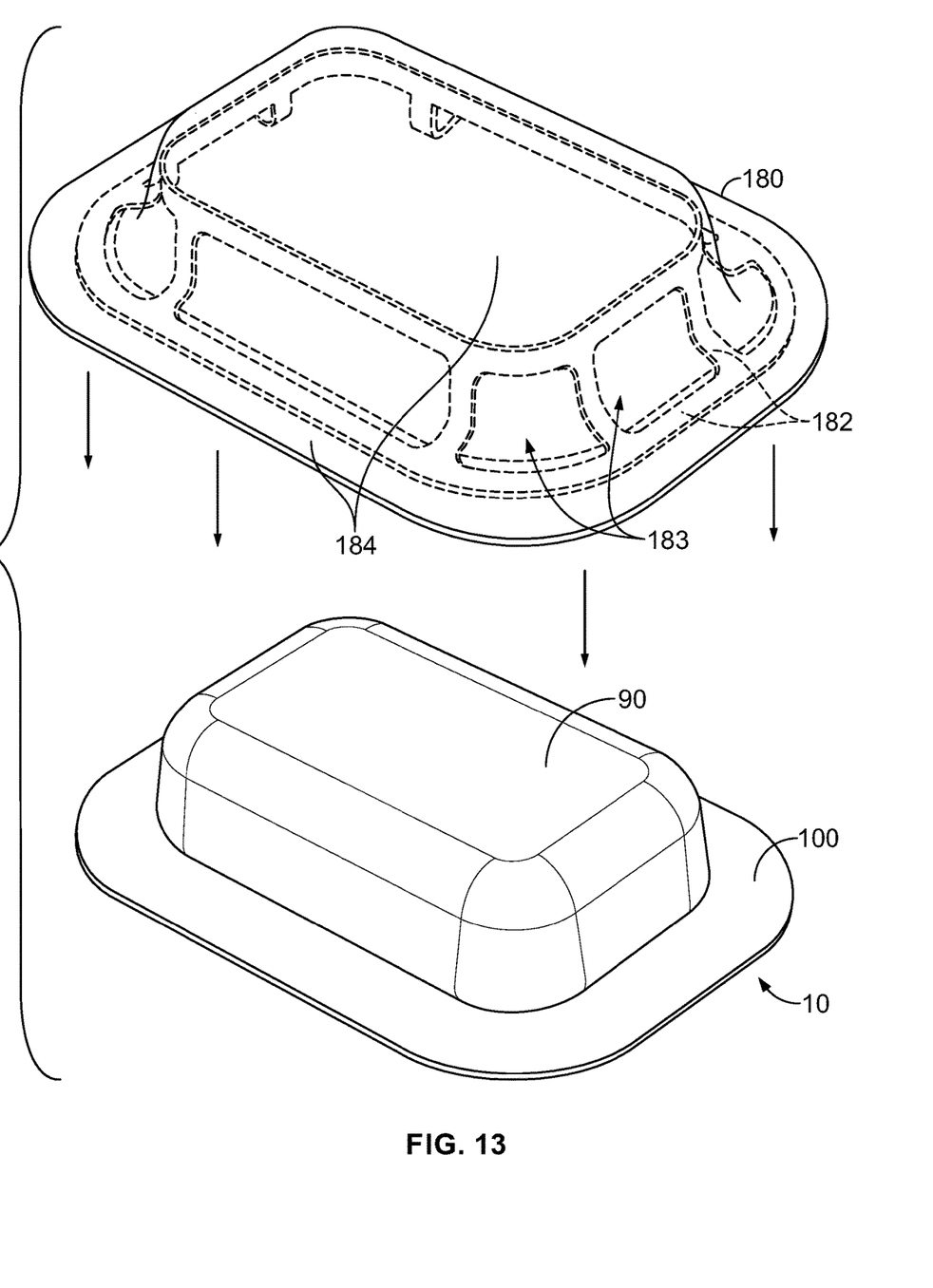
FIG. 13 is an exploded view of the drug delivery device with the adhesive module of FIG. 11.
Figure 14:
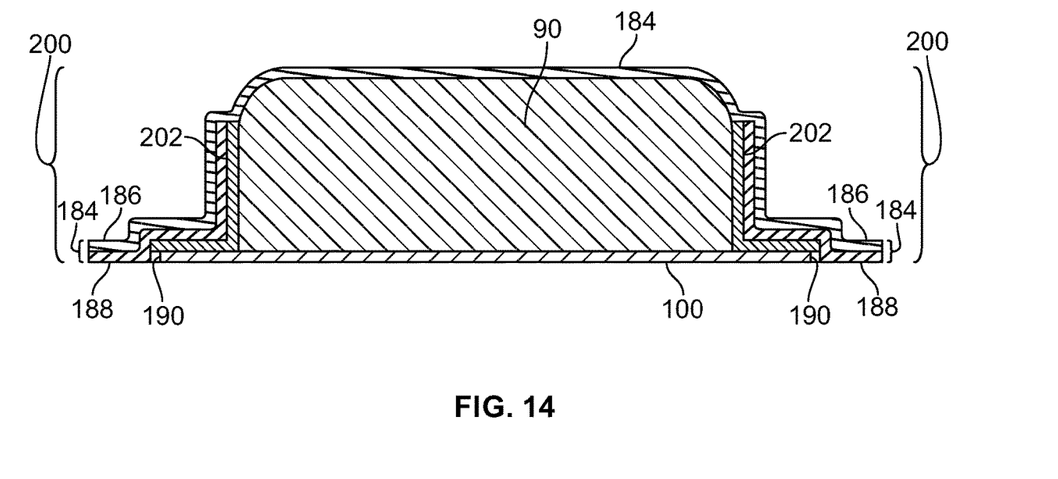
FIG. 14 is a cross-sectional side view of a drug delivery device with an alternative embodiment of an adhesive module in accordance with the present disclosure.

A further embodiment of an adhesive module in accordance with the present disclosure is shown in FIGS. 11-13. The embodiment of adhesive module 180 in FIGS. 11-13 is, in many respects, similar to the above-described embodiment of FIGS. 8-10 in that adhesive module 180 likewise includes a support structure 182. Thus, support structure 182 may be an internal frame or framework as shown in FIGS. 8-10 with a film 184 conformed thereto, as best seen in FIG. 12. More specifically, support structure 182 may be a frame or framework defining openings 183 therein. Support structure 182 may also be a screen or lattice-like structure or a solid ring to which an adhesive film 184 is attached, as will be described below. Support structure 182 may be injection molded or may be assembled from a plurality of sealed-together porous or solid sheets to form a composite structure having the desired rigidity to receive and align with drug delivery device 10.

Film 184 includes a top non adhesive surface 186 and a bottom surface 188 with adhesive applied thereon as a coating or layer. As shown in FIGS. 11 and 13, film 184 is adhered to housing 90 and provides a full covering over device 10. As in earlier embodiments, film 184 extends beyond the peripheral edge 190 of structure 182 and, once device 10 is attached to the patient, beyond the outer edge of perimeter 108 where adhesive module 180 can be directly adhered to patient's skin as shown in FIG. 12.

As discussed above, application of the on-body drug delivery device described herein utilizes a "dual adhesive" approach, namely, an adhesive on the bottom surface of the device substrate 10 and an adhesive on the bottom surface of the film that is part of the adhesive module 140, 160, 180. In as much, as the adhesive of the adhesive module likewise contacts the skin of the patient, the adhesive must be one that allows the adhesive module to remain adhered to the patient's body and, preferably, cannot be easily dislodged or separated from the patient's skin. In that regard, the adhesive of the adhesive module should be waterproof and/or resistant to degradation by perspiration. In addition, adhesive substrate should tightly conform to the skin of the patient to keep the needle of the device from dislodging. At the same time, the adhesive is not permanent and, when necessary, can be removed routinely by a medical professional in an "out-patient" procedure or even by the patient. In addition, as the adhesive may also contact and adhere to the delivery device (as in the embodiments of FIGS. 7 and 11-13) or may contact a support structure (as in the embodiments of FIGS. 8-14), the adhesive should have good adhesion to the materials used for the device 10 and support structures 164, 182. Examples of suitable adhesives for both skin and such non-skin adhesion include, but are not limited to, acrylic or acrylate compositions, synthetic rubber, hydrocolloid, silicone and the like. Thus, it should be understood that the adhesive applied to the adhesive module may be formed of the same material or materials as the adhesive applied to the adhesive applied to the substrate of the device 10 or a different material or materials.

In an alternative embodiment, rather than providing a single adhesive that is adequate for adhesion to both skin and non-skin surfaces, it is within the scope of the present disclosure for an adhesive module to include a plurality of different adhesives that are particularly configured for adhesion to either a skin or a non-skin surface. For example, an adhesive that is particularly well-suited to adhesion to a non-skin surface may be applied to a region of the adhesive module configured to engage the device 10, while a different adhesive that is particularly well-suited to adhesion of a skin surface may be applied to a region of the adhesive module configured to engage the skin of the patient. An adhesive configured to engage a surface of the device 10 may be configured to be relatively weak (allowing for dissociation of the device and adhesive module) or strong (to discourage or prevent dissociation of the device and adhesive module).

In a further alternative embodiment of the adhesive module described above and shown in FIGS. 11-13, adhesive may be applied to only a portion of the bottom surface 188 of film 184 which covers and overlies the drug delivery device. For example, the portion of film 184 that covers the device (housing 90) may be free of adhesive. As seen, for example, in FIG. 14 adhesive 188 may be applied only to the outer peripheral region of film 184 of adhesive module 200 that is coincident with support structure 202 and in contact with the patient's skin. In a further variation of this embodiment, adhesive may be applied to a peripheral region of the bottom surface 188 of film 184 that contacts only a portion of support structure 202 and the patient's skin (not shown). In still a further variation of this alternative embodiment, adhesive may be applied only to that portion of film 184 that contacts the skin of the patient (not shown).

Films 142, 166, 184 described above may be made of any flexible, stretchable material that is suited for use with the adhesives described herein. In the embodiments of FIGS. 11-13 and 14, film 184 (with or without adhesive) may conform closely to the contour of device (housing 90) as shown, for example, in FIG. 14. Alternatively, film (with or without adhesive) may cover device (housing 90) in a less conforming manner as shown, for example, in FIG. 12. Suitable film materials include, but are not limited to, polyethylene, polypropylene, polyurethanes, polyamides, polyesters, ethylene vinyl acetate, natural or synthetic polyisoprene, polybutadiene, polychloroprene, silicone, nitrile rubbers, nylon, olefin, and polyvinyl chloride.

The drug delivery devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An on-body drug delivery device comprising:
   a) a housing comprising a cover and a bottom wall;
   b) a substrate comprising a sheet of flexible material having a top surface and a bottom surface, wherein said housing is carried by said substrate and said bottom surface includes an adhesive applied thereto; and
   c) an adhesive module disposed over at least a portion of said substrate, said adhesive module including an adhesive bottom surface, said adhesive module further comprising a supporting frame surrounding said housing cover and defining a plurality of openings therein spaced around said housing cover, said supporting frame further comprising a plurality of sealed-together porous sheets.

2. The on-body drug delivery device of claim 1 wherein said substrate includes a dimension that is larger than a dimension of said housing bottom wall, said substrate including an outer edge defining a perimeter around said housing.

3. The on-body drug delivery device of claim 2 wherein said adhesive module comprises a film having a top surface and a bottom surface, and an adhesive applied to said bottom surface of said film.

4. The on-body drug delivery device of claim 3 wherein said film covers at least a portion of said housing and said substrate perimeter.

5. The on-body drug delivery device of claim 3 wherein said film completely covers said housing and said substrate perimeter.

6. The on-body drug delivery device of claim 3 wherein said film extends beyond the perimeter of said substrate.

7. The on-body drug delivery device of claim 3 wherein said film is conformed to said frame.

8. The on-body drug delivery device of claim 7 wherein said frame defines a central opening for receiving said housing.

9. The on-body drug delivery device of claim 8 wherein said adhesive module is secured to said housing.

10. The on-body drug delivery device of claim 8 wherein said adhesive module is press-fit onto said housing.

11. The on-body drug delivery device of claim 7 wherein said frame is made of a polymeric material.

12. The on-body drug delivery device of claim 3 wherein said film is made of a material polymeric material selected from the group consisting of polyvinyl chloride (PVC), polypropylene, polycarbonate and polystyrene, polyethylene, polyurethanes, polyamides, polyesters, ethylene vinyl acetate, natural or synthetic polyisoprene, polybutadiene, polychloroprene, silicone, nitrile rubbers, nylon, olefin.

13. The on-body drug delivery device of claim 3 wherein said adhesive of said adhesive module is selected from the group consisting of acrylic or acrylate compositions, synthetic rubber, hydrocolloid, silicone.

14. The on-body drug delivery device of claim 1 wherein said adhesive module adheres to at least a portion of said device and to the skin of a patient.

15. The on-body drug delivery device of claim 1 wherein said adhesive module comprises a layer of film having a bottom surface and a layer of a second adhesive applied to said film bottom layer.

16. The on-body injector of claim 1 wherein said adhesive bottom surface of said adhesive module comprises a first adhesive on one region of said bottom surface and a different adhesive on another region of said bottom surface.

17. The on-body drug delivery device of claim 1 wherein said adhesive module includes an adhesive on only a portion of said module bottom surface.

18. The on-body drug delivery device of claim 1, configured to deliver a drug comprising pegfilgrastim.

* * * * *